United States Patent [19]

Colclough et al.

[11] Patent Number: 6,072,071
[45] Date of Patent: Jun. 6, 2000

[54] PROCESS FOR THE PRODUCTION OF DINITRATE ESTERS

[75] Inventors: Martin E Colclough, Farnborough; Andrew Pelter, Swansea, both of United Kingdom

[73] Assignee: The Secretary of State for Defence in her Britannic Majesty's Goverment of the United Kingdom of Great Britain and Northern Ireland, Farnborough, United Kingdom

[21] Appl. No.: 09/254,269

[22] PCT Filed: Sep. 1, 1997

[86] PCT No.: PCT/GB97/02324

§ 371 Date: Mar. 3, 1999

§ 102(e) Date: Mar. 3, 1999

[87] PCT Pub. No.: WO98/09937

PCT Pub. Date: Mar. 12, 1998

[30] Foreign Application Priority Data

Sep. 5, 1996 [GB] United Kingdom .................... 9618483

[51] Int. Cl.[7] .................... C07C 201/02; C07C 203/04
[52] U.S. Cl. ..................... 558/480; 558/482; 558/483
[58] Field of Search .................................. 558/480, 482, 558/483

[56] References Cited

U.S. PATENT DOCUMENTS 3,549,687  12/1970  Bachman et al. .

FOREIGN PATENT DOCUMENTS 2 181 124  4/1987  United Kingdom .

*Primary Examiner*—Michael G. Ambrose
*Attorney, Agent, or Firm*—Nixon & Vanderhye

[57] ABSTRACT

1,2 and 1,3-dinitrate esters are prepared from polyols containing 1,2- or 1,3-diol fragments using an alkyl or aryl boronic acid to form a cyclic boronate ester derivative which is then reacted with dinitrogen pentoxide to directly generate the dinitrate ester. In the cyclic ester from the 1,2- or 1,3-hydroxyl groups are protected and other reactions may then be carried out on other parts of the molecule of which the fragment form a part, leaving the dinitrate ester to be produced subsequently in the final step. High yields are obtained at both stages.

8 Claims, No Drawings

PROCESS FOR THE PRODUCTION OF DINITRATE ESTERS

This application is a 371 of PCT/GB 97/02324.

The present invention relates to a method of nitrating polyols having either 1,2- or 1,3-diol fragments, which process involves, as an intermediate stage, the use of a 1,3-dioxa-2-borole (boronate ester) protecting group.

A particular problem arises in attempting the nitration of polyols having such diol fragments when they are incorporated into a polymeric chain. Polyols, even when not of high molecular weight dissolve at best only in low concentrations in either water or common organic solvents and in consequence they are difficult to completely nitrate using the common mixed acid (sulphuric/nitric acid mixture) or like methods. Even where it is possible to dissolve some of a polymeric polyol into an appropriate solvent the yields of nitrated product obtained are likely to be very low.

A further problem with conventional nitrating procedures based on mixed acids is that they are rather aggressive in character and tend to be somewhat non-specific. There is thus a considerable possibility when dealing with polymeric polyols that attack by the nitrating agent at some other location on the polymer chain will occur.

Protection of the reactive hydroxyl groups of 1,2- and 1,3-diol fragments as a cyclic phenyl boronate is well known. The procedure is shown below for a 1,2-diol which will be used hereafter in the description of the invention as a general term intended to cover the group of polyols containing either 1,2- or 1,3-diol fragments:

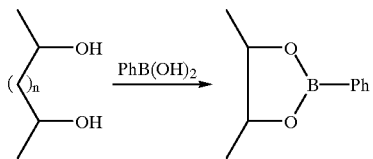

where n is 0 or 1.

Conventionally, to then obtain the dinitrate ester from the protected diol the protecting group is hydrolytically cleaved to recreate the diol and this is then treated with a conventional nitrating agent, with the disadvantages identified previously.

The applicant has now found that by use of the unconventional nitrating agent dinitrogen pentoxide it is not only possible to achieve nitration in a relatively non-aggressive manner but also without isolation of the diol. Thus it has been found possible to achieve direct nitration effectively and in good yield from a protected diol by treatment with dinitrogen pentoxide.

Accordingly the present invention provides a process for the preparation of 1,2- and 1,3-dinitrate esters from the corresponding polyol having a 1,2- or 1,3-diol fragment which comprises the steps of:

a) preparing a cyclic boronate ester derivative of the polyol by treatment of the polyol with an alkyl or aryl boronic acid;

b) reacting the cyclic boronate ester derivative with dinitrogen pentoxide under anhydrous conditions in order to form the corresponding dinitrate; and c) separating the dinitrate ester product from the boron-containing side product.

Step (a) of the process may be carried out at any suitable temperature having regard to the stability of the reactants; however the reaction will generally proceed satisfactorily at or not greatly in excess of ambient temperature. The reaction may most conveniently be carried out by mixing equimolar amounts of the diol with the boronic acid and stirring until the formation of water is evident as a separate layer. Extraction and distillation affords the boronate in excellent yield.

In an optional step between steps (a) and (b), the diol may be modified in some other reaction during which the protected hydroxyl groups are unaffected. For example a triol of general formula $HO(CH_2)_n CHOHCH_2OH$ can have the 1,2-diol fragment protected as a cyclic boronate and the free hydroxyl group can be protected as a silyl ether or as an ester such as an acetate. This gives different protecting groups for the different hydroxyl groups and thus different reactivity and the opportunity for selective deprotection.

It will be appreciated that by avoiding the presence of water, cleavage of the protecting groups and creation of the relatively insoluble hydroxyl-bearing compounds is obviated. Thus, provided that other groups sensitive to $N_2O_5$ are not present in the protected diol, the problems of unwanted side reactions and of the lack of solubility of the diols in common organic solvents are side-stepped. Furthermore the nitrating procedure according to the present invention requires only a single step whereas conventional methods require two steps.

The corresponding cyclic boronate esters are readily obtained from a 1,2- or 1,3-diol by reacting the diol with a boronic acid such as an alkyl or an aryl boronic acid. Use of the former is preferred, however, because of the tendency of the aromatic ring to be substituted with nitro-groups when the corresponding aryl cyclic esters are nitrated using $N_2O_5$. To achieve nitration of the diol in such cases, therefore, it is necessary to add an excess of the $N_2O_5$ reagent to allow for the preferential nitration of the aromatic ring. The reactions to yield cyclic boronate esters are found to proceed very efficiently in all cases attempted and the yields are in the range of 80 to 95%. The cyclic boronate esters are found to be stable in air with no evidence of decomposition to the boronic acid even after prolonged exposure.

Most conveniently the anhydrous $N_2O_5$ reagent used in the process of the present invention is a solution of $N_2O_5$ in an organic solvent such as dichloromethane. Such a solution may conveniently be prepared as described in UK Patent No. 2,252,309 granted to the present applicant. Using this solution the applicant has found that the combined deprotection and nitrating reaction will proceed quite rapidly at a temperature of as low as $-10°$ C. Typically reaction temperatures in the range of $-30°$ C. to $+25°$ C. may be utilised and the reaction will proceed to completion in the order of from 0.5 hr to 3 hrs though it will be appreciated that a combination of reaction temperature and time which is appropriate to the stability of the reactants must be employed. However, since $N_2O_5$ is itself increasingly unstable in solution at temperatures above about $+30°$ C., it will be understood that a temperature of this order forms a practical upper limit.

The use of such a mild and specific nitration procedure is extremely advantageous since it will permit the nitration of diols which might, under more conventional nitrating procedures, undergo attack at other portions of the diol molecule. Thus, subject only to the absence of any group which is susceptible to attack by the $N_2O_5$ reagent at the relatively low temperatures required and provided that the protected diol is soluble in the solvent chosen, a very wide range of 1,2- and 1,3-diols may be nitrated by the process of this invention.

It is desirable that the boronic acid starting material is recovered in a final step of the process because this material will often constitute one of the most expensive reagents for the process and is therefore advantageously recycled.

The nitrated products of polymeric diols are energetic materials which have important applications in the fields of explosives and propellants either directly or as precursors for such materials.

The present invention will now be further described with reference to the following examples.

REACTION PROTOCOL
1. Esterification

The reaction involved in this step may be generally represented as follows:

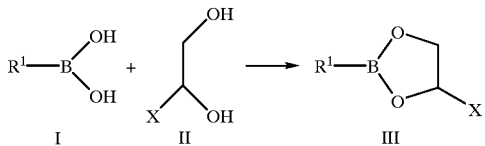

where $R^1$ is a butyl or a phenyl group and X is one of the following substituents: $(CH_2)_nOH$ (a); $(CH_2)_nOCOCH_3$ (b); $(CH_2)_nOCOPh$ (c); $(CH_2)_nCH_3$ (d); $(CH_2)_nPh$ (e); $(CH_2)_nOSi(Me)_2Bu^t$ (f) or $(CH_2)_nOSiPr_3$ (g) and where n is 2, 4 or 6.

Typically, either butyl or phenyl boronic acid is added to an equimolar amount of the diol or triol. As an example, in the esterification of 1,2,6-trihydroxyhexane (compound IIa, n=4) with n-butyl boronic acid (compound I, $R^1$=n-butyl), a dry single necked 250 ml round bottomed flask was charged with n-butyl boronic acid (10.2 g, 100 mmol) and 1,2,6-trihydroxyhexane (14.1 g, 105 mmol). The flask was flushed with argon before sealing with a rubber septum. Dry diethyl ether (110 ml) was added and the reaction stirred at room temperature. The reaction was found to go to completion after 3–4 hrs when the foundation of water could be observed as a separate layer. At this point an equal quantity of pentane (110 ml) was added followed by a quantity of magnesium sulphate sufficient to mop up all of the water. The cyclic boronate ester product was isolated by simply filtering the solution, evaporating off the solvent and distilling the product under reduced pressure to give 18.6 g, 93% yield of the pure cyclic boronate ester (compound IIIa, n=4).

A number of such preparations was carried out. The yields obtained for each product are set out in Table 1 below and are seen to be consistently high. The products were found to be analytically pure and no evidence of polymerisation was found when using the triol (product IIIa).

Similarly the esterification reaction of 1,3-diols was also investigated with n-butyl boronic acid; a typical example of 2-butyl-2-ethyl-1,3-propanediol (compound IVn) is described. The general reaction procedure is illustrated below:

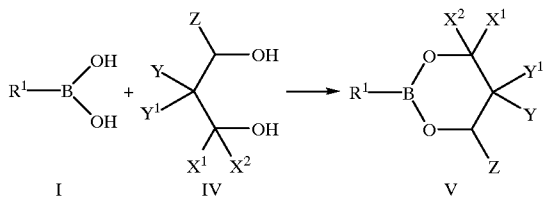

where $R^1$ is a butyl or phenyl group and the other substituents are selected as follows: $X^1=X^2=Y=Y^1=Z=H$ (h); $X^1=CH_3$, $X^2=Y=Y^1=Z=H$ (i); $X^1=CH_3$, $X^2=Y=Y^1=H$, $Z=CH_3$ (j); $X^1=X^2=CH_3$, $Y=Y^1=H$, $Z=CH_3$ (k); $X^1=X^2=H$, $Y=Y^1=CH_3$, $Z=(CH_3)_2CH$ (l); $X^1=X^2=H$, $Y=CH_2CH_2CH_3$, $Y^1=CH_3$, $Z=H$ (m); $X^1=X^2=H$, $Y=CH_2CH_2CH_2CH_3$, $Y^1=CH_2CH_3$, $Z=H$ (n); $X^1=X^2=H$, $Y=CH_2CH_3$, $Y^1CH_3$, $Z=H$ (o); and $X^1=X_2=H$, $Y=CH_2CH_2CH_3$, $Y^1=CH_2CH_3$, $Z=H$ (p).

A dry single necked 50 ml round bottomed flask was charged with n-butyl boronic acid (10 ml of 1.0 M soln. in ether, 10 mmol) and 2-butyl-2-ethyl-1,3-propanediol ((IVn); 12 ml of 1.0 M soln. in ether, 12 mmol). The flask was flushed with argon before sealing with a rubber septum. The reaction was found to go to completion after 3–4 hrs when the formation of water could be observed as a separate layer. At this point an equal amount of pentane (20 ml) was added followed by a quantity of magnesium sulphate sufficient to mop up all of the water. The boronic ester product was isolated by simply filtering the solution, evaporating off the solvent and distilling the product under reduced pressure to give 2.24 g, 98% yield of the pure cyclic boronic ester Vn. The yields obtained for various 1,3-diols are shown below in Table 2.

2. Nitration

A typical example using compound IIIb (n=2; $R^1$=butyl) is as follows.

To a 500 ml nitrogen flushed dry 3-necked round bottomed flask fitted with an alcohol thermometer and magnetic stirrer and dropping funnel was added a solution of $N_2O_5$ (36.7 g, 0.34 mol) in dichloromethane (250 ml), previously prepared from $N_2O_4$ and $O_3$ at –20° C. All outlets were sealed with rubber septa. 18.2 g, 85 mmol of the cyclic boronate ester (compound IIIb (n=2)) prepared in the manner described above was introduced as a solution in dry dichloromethane (50 ml) via the dropping funnel over 10 mins. between –10 to –20° C. After the addition the mixture was allowed to stir for 3–4 hrs between –5 to –20° C. under nitrogen before quenching the reaction by the addition of a saturated solution of sodium bicarbonate (3×150 ml). Separation of the layers, drying of the dichloromethane layer with magnesium sulphate, filtration and removal of the solvent gave 31.1 g of crude compound VIb (n=2) (see below). The crude mixture was purified by flash chromatography through a silica column using a gradient eluent system starting off at 100% petroleum ether (40–60° C.) and gradually increasing to 100% dichloromethane to give 17.28 g, 85% yield of pure compound VIb (n=2). Note that due to the explosive nature of nitrate esters distillation of the products is not recommended.

Similar nitration procedures can be carried out on the protected 1,3 diols (V). A typical nitration of a protected 1,3-diol e.g. 2-ethyl-2-butyl-1,3-propanediol (Vn) is as follows.

To a 200 ml nitrogen flushed dry 3-necked round bottomed flask fitted with an alcohol thermometer and magnetic stirrer and dropping funnel was added a solution of $N_2O_5$ (0.96 g, 8.94 mmol) in dichloromethane (100 ml), previously prepared from $N_2O_4$ and $O_3$ at –20° C. All outlets were sealed with rubber septa. 0.51 g, 2.23 mmol of the cyclic boronic ester Vn, prepared as described above was introduced as a solution in dry dichloromethane (50 ml) via the dropping funnel over 10 mins. between –10 to –20° C. After addition the mixture was allowed to stir for 3–4 hrs between –5 to –10° C. under nitrogen before quenching the reaction by the addition of a saturated solution of sodium bicarbonate (3×50 ml). Separation of the layers, drying of the dichloromethane with magnesium sulphate, filtration and removal of the solvent gave 0.71 g of crude VIIn. The crude mixture was purified by flash chromatography through a silica column using a gradient eluent system of 100% petroleum ether (40–60° C.) to 100% dichloromethane to give 0.51 g, 89% yield of pure VIIn. The results for the various protected 1,3-diols are shown in Table 2 below.

Although the nitration can be carried out between −20° C. to +30° C. the ideal temperature is that used above mainly due to the instability of $N_2O_5$ at higher temperatures. The acetyl group in compound IIIb (n=2) does not undergo nitration under normal conditions. However reactions carried out where the mixture is allowed to warm up to ambient temperature during the course of the reaction were found to contain appreciable amounts of trinitrate ester (compound VI where X represents the group $(CH_2)_2ONO_2$). At higher temperatures decomposition of $N_2O_5$ to nitric acid occurs readily in solution to give a mixture of $N_2O_5$ and nitric acid which is a more powerful nitrating agent than $N_2O_5$ alone. Acetyl groups are readily nitrated in this medium, hence the presence of the trinitrate ester. Under normal nitrating conditions 1.5 equivalents of $N_2O_5$ are sufficient per mole of substrate, however in some of the above cases 2 equivalents of $N_2O_5$ gave better yields. When the ester was a phenyl-boronic ester three equivalents of $N_2O_5$ were used to allow for preferential nitration of the aromatic ring.

The reaction process for nitration of cyclic boronic esters derived from 1,2- and 1,3-diols ay be represented by the following respective equations:

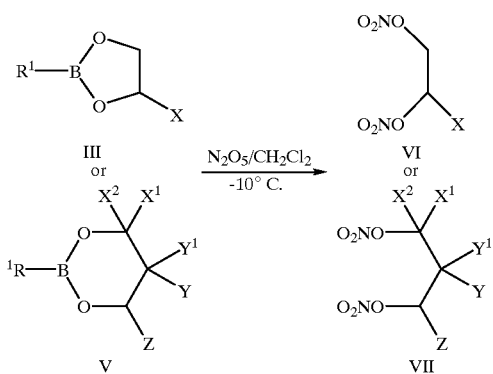

where $R^1$ is n-butyl or is phenyl and X represents one of the following substituents: $(CH_2)_nOH$ (a); $(CH_2)_nOCOCH_3$ (b); $(CH_2)_nOCOPh$ (c); $(CH_2)_nCH_3$ (d); $(CH_2)_nPh$ (e); $(CH_2)_nOSi(Me)_2Bu^t$ (f) and $(CH_2)_nOSiPr_3$ (g) and n is 2,4 or 6; and where $X^1=X^2=Y=Y^1=Z=H$ (h); $X^1=CH_3$, $X^2=Y=Y^1=Z=H$ (i); $X^1=CH_3$, $X_2=Y=Y^1=H$, $Z=CH_3$ (j); $X^1=X^2=CH_3$, $Y=Y^1=H$, $Z=CH_3$ (k); $X^1=X^2=H$, $Y=Y^1=CH_3$, $Z=(CH^3)_2CH$ (l); $X^1=X^2=H$, $Y=CH_2CH_2CH_3$, $Y^1=CH_3$, $Z=H$ (m); $X^1=X^2=H$, $Y=CH_2CH_2CH_3$, $Y^1=CH_2CH_3$, $Z=H$ (n); $X^1=X^2=H$, $Y=CH_2CH_3$, $Z=H$, (o); or $X^1=X^2=H$, $Y=CH_2CH_2CH_3$, $Y^1=CH_2CH_3$, $Z=H$ (p).

The yields obtained for a series of products of formula VI are set out table 1 below and it can be seen that they are high with the exception of silyl derivatives. Examination of the products of nitration in this case suggested that rather than producing a nitrated diol or triol, cleavage of the silyl moiety of the cyclic boronate ester had occurred.

The yields obtained for a series of products of formula VII are set out in Table 2 below and it can be seen that they are all high. The starting materials in each of these cases are alkyl substituted but analogy with the functional compounds used for the reactions with 1,2-diols indicates that the same functional group tolerance will be observed.

Where $R^1$ is phenyl as explained earlier it is necessary to use a three-fold amount of $N_2O_5$ since two equivalents are preferentially used up in the nitration of the aromatic ring before nitration of the cyclic boronic ester takes place. Likewise, where the side chain X contained an aromatic ring as with compound III(e), a further two-fold excess of $N_2O_5$ is required to compensate for preferential attack on the aromatic ring in the side chain. In the case of the triol III(a), one further equivalent of $N_2O_5$ was needed to effect nitration of all of the hydroxyl groups. Good yields of the trinitrate ester were then however obtained.

RESULTS

Yields obtained in various preparations are set out in Tables 1 and 2 below.

TABLE 1

| Example | $R^1$ | diol or triol i.e. X = | n | isolated yield of purified cyclic ester III (%) | isolated yield of purified nitrate ester VI (%) |
|---|---|---|---|---|---|
| 1 | Ph | a | 2 | 81 | 82* |
| 2 | Ph | a | 4 | 86 | 84* |
| 3 | Ph | a | 8 | 83 | 88* |
| 4 | Ph | b | 2 | 92 | 81 |
| 5 | Ph | b | 4 | 91 | 78 |
| 6 | Ph | b | 8 | 87 | 83 |
| 7 | Ph | c | 2 | 93 | |
| 8 | Ph | c | 4 | 92 | |
| 9 | Ph | c | 8 | 91 | |
| 10 | Ph | d | 5 | 81 | 87 |
| 11 | Ph | e | 2 | 86 | 76~ |
| 12 | Ph | f | 2 | | 0 |
| 13 | Ph | f | 4 | | 0 |
| 14 | Ph | f | 8 | | 0 |
| 15 | Ph | g | 2 | | 0 |
| 16 | Ph | g | 4 | | 0 |
| 17 | Ph | g | 8 | | 0 |
| 18 | Bu | a | 2 | 92 | 89* |
| 19 | Bu | a | 4 | 93 | 82* |
| 20 | Bu | a | 8 | 88 | 85* |
| 21 | Bu | b | 2 | 93 | 85 |
| 22 | Bu | b | 4 | 98 | 94 |
| 23 | Bu | b | 8 | 94 | 86 |
| 24 | Bu | c | 2 | 87 | |
| 25 | Bu | c | 4 | 91 | |
| 26 | Bu | c | 8 | 89 | |
| 27 | Bu | d | 5 | 91 | 93 |
| 28 | Bu | e | 2 | 96 | 82~ |
| 29 | Bu | f | 2 | | 0 |
| 30 | Bu | f | 4 | | 0 |
| 31 | Bu | f | 8 | | 0 |
| 32 | Bu | g | 2 | | 0 |
| 33 | Bu | g | 4 | | 0 |
| 34 | Bu | g | 8 | | 0 |

Notes:
*a further one equivalent of $N_2O_5$ was required to allow for nitration of the third OH group
~a further two equivalents of $N_2O_5$ were required to allow for nitration of the phenyl ring

TABLE 2

| Example | $R^1$ | $X^1$ | $X^2$ | Y | $Y^1$ | Z | isolated yield of purified cyclic ester V (%) | isolated yield of purified nitrate ester VII (%) |
|---|---|---|---|---|---|---|---|---|
| h | Bu | H | H | H | H | H | 96 | 96 |
| i | Bu | Me | H | H | H | H | 93 | 81 |
| j | Bu | Me | H | H | H | H | 98 | 81 |

TABLE 2-continued

| Example | R$^1$ | X$^1$ | X$^2$ | Y | Y$^1$ | Z | isolated yield of purified cyclic ester V (%) | isolated yield of purified nitrate ester VII (%) |
|---|---|---|---|---|---|---|---|---|
| k | Bu | Me | Me | H | H | H | 94 | 84 |
| l | Bu | H | H | Me | Me | Me$_2$CH | 96 | 68 |
| m | Bu | H | H | Pr | Me | H | 99 | 79 |
| n | Bu | H | H | Bu | Et | H | 98 | 89 |
| o | Bu | H | H | Et | Me | H | 96 | 80 |
| p | Bu | H | H | Pr | Et | H | 93 | 83 |

What is claimed is:

1. A process for the preparation of 1,2- and 1,3-dinitrate esters from a corresponding polyol having a 1,2- or 13-diol fragment that comprises the steps of:

(a) preparing a cyclic boronate ester derivative of the polyol by treatment of the polyol with an alkyl or aryl boronic acid;

(b) reacting the cyclic boronate ester derivative with dinitrogen pentoxide under anhydrous conditions in order to form the corresponding dinitrate; and (c) separating the dinitrate ester product from the boron-containing side product.

2. The process as claimed in claim 1 wherein the boronic acid is an alkyl boronic acid.

3. The process as claimed in claim 1 wherein the boronic acid is phenyl boronic acid.

4. The process as claimed in claim 1 wherein step (a) is carried out at or that ambient temperature.

5. The process as claimed in claim 1 wherein step (b) is carried out using a solution of dinitrogen pentoxide in an organic solvent.

6. The process as claimed in claim 5 wherein the organic solvent is dichloromethane.

7. The process as claimed in claim 1 wherein step (b) is carried out at a temperature in the range of −30° to +25° C.

8. The process as claimed in claim 1 that includes the further step of recovering the boronic acid starting material.

* * * * *